United States Patent [19]

Jacoulet et al.

[11] Patent Number: 5,207,575
[45] Date of Patent: May 4, 1993

[54] DEVICE FOR CONNECTING A DENTISTRY HANDPIECE OR CONTRA-ANGLE ON A SUPPORT

[75] Inventors: Jean-Paul Jacoulet, Besancon; Jacques Pernot, Geneuille, both of France

[73] Assignee: Micro Mega SA, Besancon, France

[21] Appl. No.: 616,223

[22] Filed: Nov. 20, 1990

[30] Foreign Application Priority Data

Nov. 27, 1989 [FR] France .................. 89 15760

[51] Int. Cl.⁵ .................................. A61C 1/08
[52] U.S. Cl. .............................. 433/126; 433/29
[58] Field of Search ......................... 433/126, 29

[56] References Cited

U.S. PATENT DOCUMENTS

| | | | |
|---|---|---|---|
| 4,182,038 | 1/1980 | Fleer | 433/126 X |
| 4,217,101 | 8/1980 | Loge | 433/126 |
| 4,278,429 | 7/1981 | Straihammer et al. | 433/126 |
| 4,403,959 | 9/1983 | Hatakeyama | 433/126 |
| 4,507,085 | 3/1985 | Mosimann et al. | 433/126 |
| 4,568,284 | 2/1986 | Stankiewicz | 433/126 |
| 4,661,060 | 4/1987 | Strohmaier | 433/126 X |
| 4,669,982 | 6/1987 | Fleer | 433/126 X |
| 4,720,266 | 1/1988 | Leonard et al. | 433/126 |
| 5,074,785 | 12/1991 | Malata, Jr. | 433/126 X |

FOREIGN PATENT DOCUMENTS 2584918 1/1987 France .................. 433/126

*Primary Examiner*—Gene Mancene
*Assistant Examiner*—Nicholas D. Lucchesi
*Attorney, Agent, or Firm*—Weiser & Associates

[57] ABSTRACT

A support for a dentistry handpiece or contra-angle is connected to a dental unit, such as a motor, including apparatus for the supply of water and air for spraying the working point of the supported handpiece of contra-angle and, if desired, apparatus for supplying electric current to bulbs situated in the head of the handpiece or contra-angle for lighting in the working point and/or fibre optics. The rear face of the support is provided with a projecting ring of insulating material and the motor includes an annular hollow form for receiving the ring when the support is mounted to the motor.

10 Claims, 3 Drawing Sheets

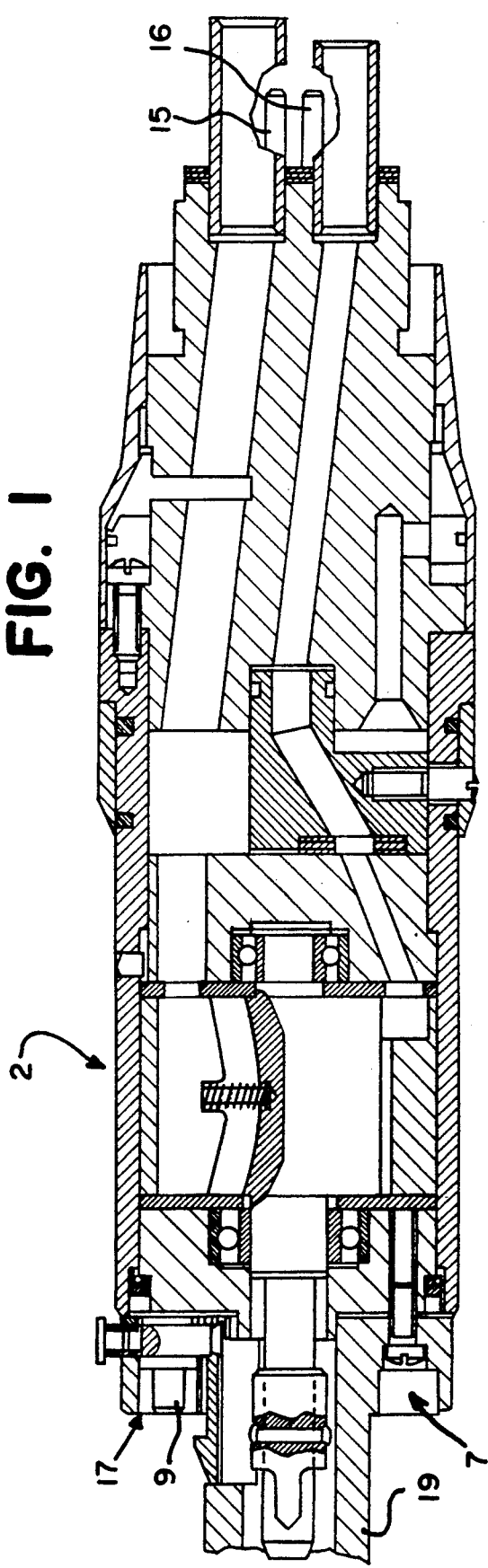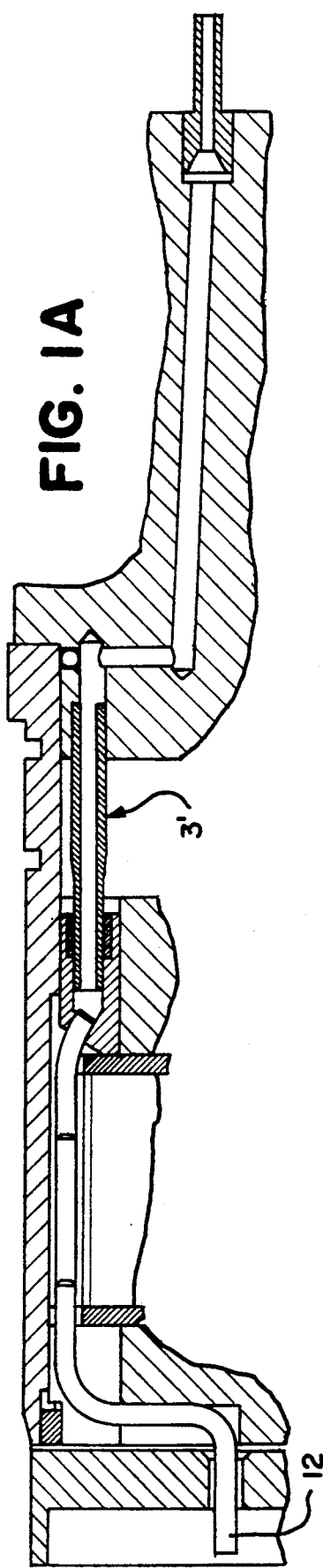

DEVICE FOR CONNECTING A DENTISTRY HANDPIECE OR CONTRA-ANGLE ON A SUPPORT

The present invention relates to a device for connecting a dentistry handpiece or contra-angle on the support connecting them to the dental unit, such as a motor, comprising means for the supply of water and air for the spray watering of the working point of the instrument which it supports and, if appropriate, means for supplying electric current to bulbs situated in the handpiece or the contra-angle for the purposes of lighting the working point, and also, if appropriate, supply means for fibre optics.

The invention also relates individually to the handpieces and the supports thus equipped.

The technique of dentistry handpieces provided with devices for integrated air-water spraying and/or a device for lighting the working site of the instrument is now wide-spread in the world of dentistry.

The introduction of these complementary functions has necessitated the creation of a connecting device between, for example, the motors and the handpieces or contra-angle.

At a time when the supply cords connecting the handpiece to the dental unit were of an excessive rigidity, attempts were made to produce rotary devices which lead to the use of leakproof connections based on O-ring seals, from which there is a risk of wearing or of electrical contacts rubbing, which are also a source of breakdown due to wearing.

French Patent 2,525,467 presents a device in which there is no rotation of the contra-angle relative to the handpiece, but with the disadvantage that the spray conduits pass from the motor between O-ring seals which, upon each positioning of the contra-angle on the motor, are subjected to aggression leading finally to a risk of leakage.

The aim of the invention is to overcome these disadvantages of the connecting devices of the prior art by ensuring additionally that the special modified motors according to the invention can receive in a compatible manner conventional handpieces not in accordance with the invention during operation of said handpieces (sic).

According to the invention, this result is achieved with a device for connecting a dentistry hand-piece or contra-angle on the support connecting them to the dental unit, such as a motor, comprising means for the supply of water and air for the spray watering of the working point of the instrument which it supports and, if appropriate, means for supplying electric current to bulbs situated in the handpiece or contra-angle for the purposes of lighting the working point, and also, if appropriate, supply means for fibre optics, characterized in that the rear face of the handpiece is provided with a projecting ring made of insulating material and in that the motor possesses an annular hollow form receiving the said ring when the handpiece is mounted on the motor.

According to an advantageous embodiment, the ring is provided with a notch and the motor with a lug designed to interlock in order to ensure the relative angular positioning of the two elements, and the channels for water and air emerge from the ring in a longitudinal fashion, the motor having, opposite each other, tubes engaging in the holes emerging from the ring.

The invention will be better understood with the aid of the description given hereinbelow of one embodiment given by way of non-limiting example, reference being made to the attached diagrams in which.

Figure 1B:
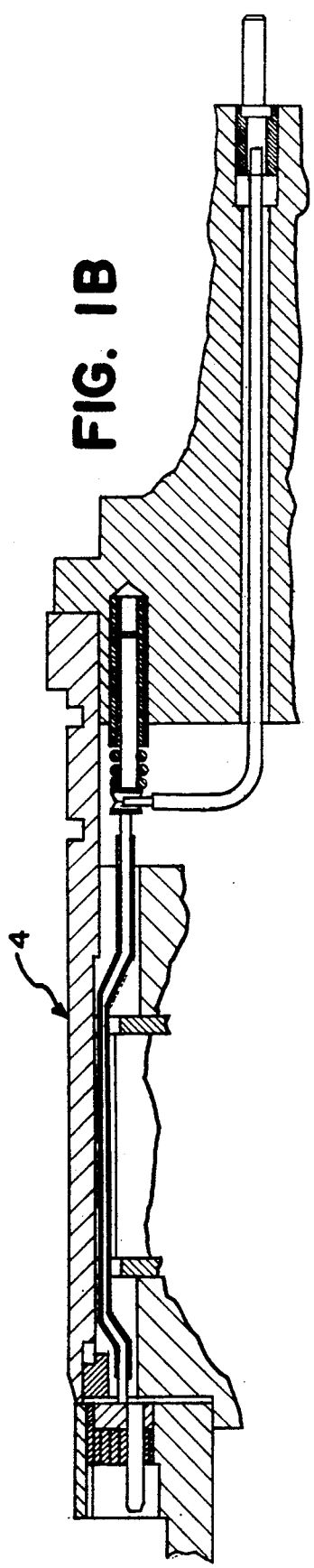
FIG. 1 is a longitudinal cutaway view of a motor with a connecting device according to the invention, with details of the spray pathway and electric pathway in 1A and 1B, respectively.

The device of the invention is intended to connect a handpiece or contra-angle, generally designated (1), to a support (2), in this case a motor. The support could be of any other type, connected to a dental unit, without departing from the scope of the invention.

The means inside the piece (1) and the motor (2) which permit the passage through the latter of air and water conduits (3, 3') and electricity conduits (4, 4') are known to the person skilled in the art and will not be described in more detail.

According to the invention, the rear face (5) of the handpiece comprises a ring (6) of insulating material, preferably a mouldable material, projecting relative to the plane of the said rear face, and the support, namely in this case the motor (2), possesses a corresponding annular hollow receiving form (7) receiving the said ring when the handpiece is fitted into the motor.

Figure 2A:
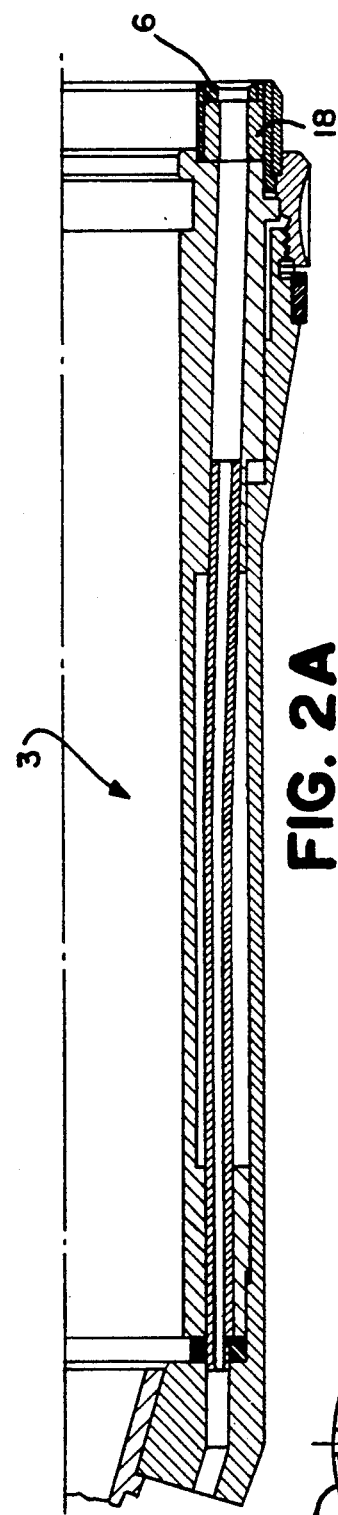
FIGS. 2, 2A and 2B are the corresponding views of a handpiece with a connecting device according to the invention, with FIG. 2C which is a view of the handpiece from the connecting side.
Figure 2C:
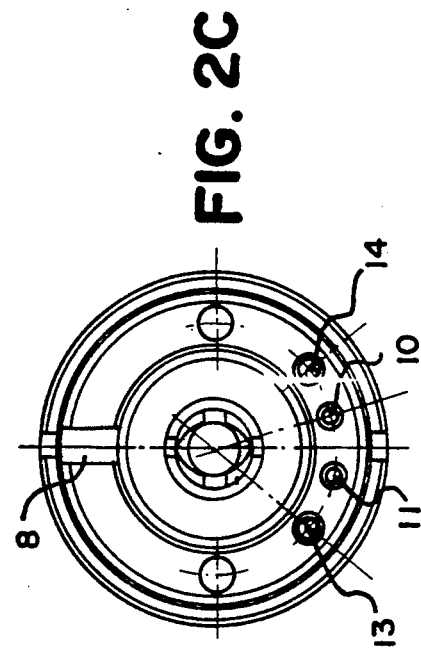
Figure 2B:
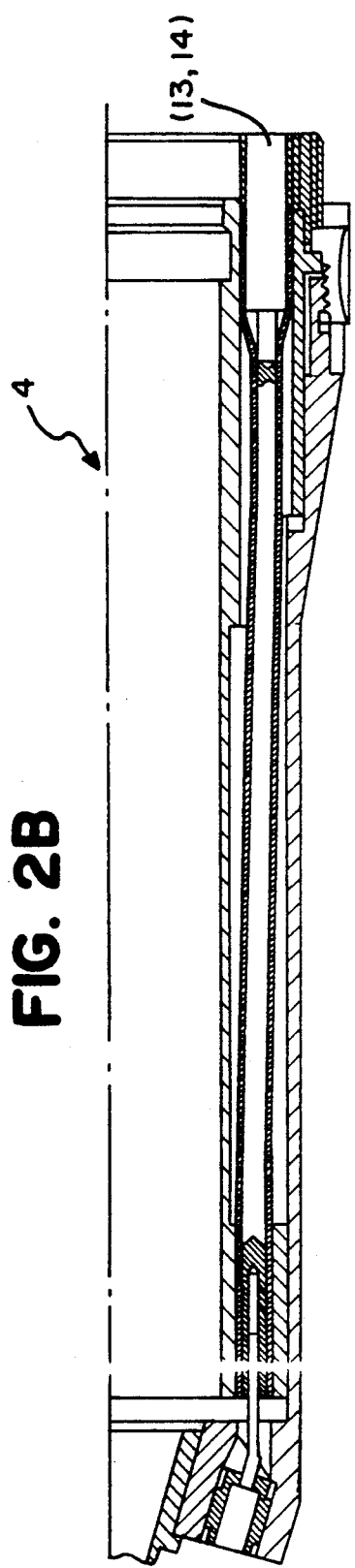
Figure 2:
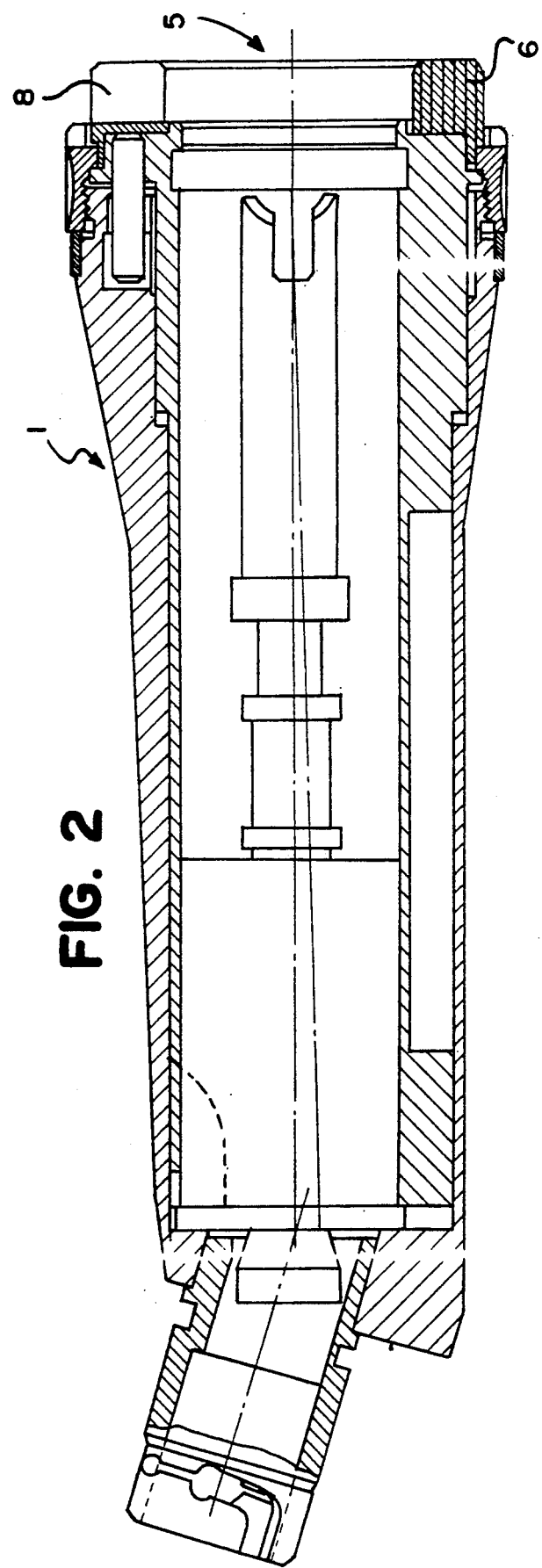

The ring (6) is advantageously provided with a notch (8), which can be seen in FIG. 2C, and the motor is provided with a lug (9) which are designed to interlock in order to ensure the correct relative angular positioning of the two pieces (1) and (2).

Thus, the respective water (10) and air (11) channels emerge from the ring longitudinally, the motor comprising, opposite each other, tubes (12) engaging in the outlets (10) and (11).

According to an important characteristic of the invention, the handpiece is provided with two female contacts (13, 14) positioned axially. The motor possesses two male contacts (15, 16) in the form of rods penetrating the said female contacts and thus providing for the electrical connection.

For the purposes of protecting the tubes and the contacts of the motor, it will be ensured that these do not project beyond the annular groove (7). This also makes it possible to fit any other conventional handpiece.

More specifically, it will be ensured that the face (17) of the motor which is to receive the handpiece is such that the motor can receive, without destruction of the tubes and/or of the contacts or creation of a short-circuit between contacts, handpieces without spray or light whose coupling is in accordance with ISO standard 3964.

According to an advantageous characteristic of application of the invention, it will be ensured that the leakproofness between the tubes (12) of the motor and the air/water orifices (10, 11) of the handpiece is provided for by a cylindrical seal (18) housed in the ring (6) and compressed by it during assembly.

Finally, it will be ensured that the motor is equipped with a connecting bush (19) in accordance with ISO standard 3964.

The bush is integral with the front face of the motor, and this single piece is made of a mouldable insulating material.

We claim:

1. A device connecting a support for a dentistry handpiece or contra-angle to a dental unit, wherein the dental unit includes means for supplying water and air for spraying a working point, and means for supplying lighting to head portions of the handpiece or contra-angle, and wherein the connecting device comprises:
   a ring formed of an insulating material and projecting from rear face portions of the support;
   an annular hollow formed in the dental unit for receiving the ring when the support is mounted to the dental unit;
   a notch formed in the ring and a lug projecting from the dental unit, for interlocking engagement to establish and maintain a relative angular positioning of the support relative to the dental unit;
   water and air channels longitudinally emerging from the ring, for engaging water and air tubes longitudinally extending from the dental unit, for supplying the water and air for spraying the working point; and
   female contacts radially positioned on the support, for engaging male contacts axially extending from the dental unit, for supplying the lighting to the head portions of the handpiece or contra-angle.

2. The connecting device of claim 1 wherein the dental unit is a motor for operating the handpiece or contra-angle.

3. The connecting device of claim 1 wherein the tubes and the male contacts do not project beyond the annular hollow.

4. The connecting device of claim 1 wherein the tubes and the channels are placed in leakproof engagement by cylindrical seals received within the ring, for compression by the tubes when the support is mounted to the dental unit.

5. The connecting device of claim 1 wherein the dental unit includes a connecting bush formed in accordance with ISO standard 3964, and integral with front face portions of the dental unit.

6. The connecting device of claim 5 wherein the integral connecting bush is formed of a moldable insulating material.

7. A dentistry handpiece or contra-angle which comprises a connecting element in accordance with claim 1.

8. The connecting device of claim 1 wherein the ring is attached to the rear face portions of the support.

9. The connecting device of claim 1 wherein the notch cuts across the ring and the lug extends across the annular hollow.

10. A device connecting a support for a dentistry handpiece or contra-angle to a dental unit, wherein the dental unit includes means for supplying water and air for spraying a working point, and means for supplying lighting to head portions of the handpiece or contra-angle, and wherein the connecting device comprises:
   a ring formed of an insulating material, attached to and projecting from rear face portions of the support;
   an annular hollow formed in the dental unit for receiving the ring when the support is mounted to the dental unit;
   a notch cutting across the ring and a lug extending across the annular hollow and projecting from the dental unit, for interlocking engagement to establish and maintain a relative angular positioning of the support relative to the dental unit;
   water and air channels longitudinally emerging from the ring, for engaging water and air tubes longitudinally extending from the dental unit, for supplying the water and air for spraying the working point; and
   female contacts radially positioned on the support, for engaging male contacts axially extending from the dental unit, for supplying the lighting to the head portions of the handpiece or contra-angle;
   wherein the tubes and the male contacts do not project beyond the annular hollow, and wherein the tubes and the channels are placed in leakproof engagement by cylindrical seals received within the ring, for compression by the tubes when the support is mounted to the dental unit.

* * * * *